United States Patent [19]

Roberts et al.

[11] 4,324,648
[45] Apr. 13, 1982

[54] CRACKING CATALYST POISONS PASSIVATED WITH TIN COMPOUNDS PLUS BOTH SULFUR AND PHOSPHORUS

[75] Inventors: John S. Roberts; Brent J. Bertus; Dwight L. McKay; H. Wayne Mark, all of Bartlesville, Okla.

[73] Assignee: Phillips Petroleum Company, Bartlesville, Okla.

[21] Appl. No.: 132,719

[22] Filed: Mar. 24, 1980

[51] Int. Cl.³ ............................................. C10G 11/05
[52] U.S. Cl. .............................. 208/114; 208/52 CT; 208/113; 208/120; 252/411 R
[58] Field of Search ................. 208/120, 113–114, 208/52 CT

[56] References Cited

U.S. PATENT DOCUMENTS

| | | | |
|---|---|---|---|
| 2,129,693 | 9/1938 | Houdry | 208/120 |
| 2,449,050 | 9/1948 | Bond et al. | 208/114 |
| 2,758,097 | 8/1956 | Doherty et al. | 252/413 |
| 2,901,419 | 8/1959 | Brill | 208/119 |
| 2,921,018 | 1/1960 | Helmers et al. | 208/114 |
| 2,977,322 | 3/1961 | Varvel et al. | 252/411 |
| 3,904,550 | 9/1975 | Pine | 208/217 X |
| 4,020,011 | 4/1977 | Nishikawa et al. | 252/441 |
| 4,025,458 | 5/1977 | McKay | 252/416 |
| 4,101,417 | 7/1978 | Mitchell et al. | 208/120 |
| 4,167,471 | 9/1979 | Bertus et al. | 208/113 X |
| 4,226,700 | 10/1980 | Broom | 208/48 AA |

FOREIGN PATENT DOCUMENTS

| | | | |
|---|---|---|---|
| 729167 | 3/1966 | Canada | 208/114 |
| 1506773 | 4/1978 | United Kingdom | 252/441 |
| 1510155 | 5/1978 | United Kingdom | 252/437 |

*Primary Examiner*—Delbert E. Gantz
*Assistant Examiner*—G. E. Schmitkons

[57] ABSTRACT

Deposits on a cracking catalyst are passivated by contacting the cracking catalyst with tin and at least one of phosphorus or sulfur.

20 Claims, No Drawings

CRACKING CATALYST POISONS PASSIVATED WITH TIN COMPOUNDS PLUS BOTH SULFUR AND PHOSPHORUS

BACKGROUND OF THE INVENTION

This invention relates to the art of the catalytic cracking of hydrocarbons. In another aspect, the invention relates to reducing the detrimental effects of contaminating deposits on a cracking catalyst. In still another aspect, the invention relates to the passivation of metals on cracking catalysts.

In most conventional catalytic cracking processes in which hydrocarbon feedstocks are cracked to produce light distillates a gradual deterioration of the catalyst occurs. Some of this deterioration is attributable to the deposition on the catalyst of contaminants contained within the feedstock. The deposition of these contaminants, which include nickel, vanadium and iron, tends to adversely affect the cracking process by decreasing conversion of the feedstock to cracked products, decreasing production of gasoline and increasing yields of hydrogen and coke.

It is known in the art that the adverse effects of catalyst contamination can be partially offset by treating the cracking catalyst with passivating agents, for example, antimony and its compounds. Treatment of the cracking catalyst with antimony is extremely desirable in that all four indicia of catalyst deterioration due to deposits of contaminants are improved. Conversion and selectivity to gasoline increase, while hydrogen and coke production decrease. Other passivating agents do not result in improvement in all four indications of undesirable cracking behavior due to deposits of contaminants on the catalyst. In fact, some passivating agents actually worsen one or more of the indicators of undesirable cracking behavior, for example, by decreasing conversion, but are still termed a passivating agent because they improve another of the indicators, for example, by reducing the production of hydrogen.

Cracking catalysts which are resistant to acquiring undesirable cracking behavior when contaminants are deposited thereon from the feedstock are very desirable in that they make possible the economic conversion of poor quality feedstocks to gasoline and other light hydrocarbons. Because poor quality feedstocks are in relative abundance, there is a need for new and improved passivating agents which impart more desirable cracking characteristics to contaminated cracking catalysts. There is also a need for passivating agents which impart to cracking catalysts resistance to becoming adversely affected by contamination from the feedstock. Because of environmental laws which might restrict the use of certain passivating agents, it is also extremely desirable to provide alternative passivating agents so that contaminated oils can continue to be economically cracked.

OBJECTS OF THE INVENTION

It is thus an object of this invention to counteract the effects of metals deposition on a cracking catalyst.

It is another object of this invention to at least partially reactivate a cracking catalyst which has been partially deactivated by deposits of contaminants thereon.

It is a further object of this invention to provide an improved process which is particularly useful for cracking hydrocarbon feedstocks containing contaminating metals.

These and other objects of the present invention will be more fully explained in the following detailed description of the invention and the appended claims.

SUMMARY OF THE INVENTION

According to one embodiment of the invention, a cracking catalyst is contacted with a tin source and at least one of a phosphorus source and a sulfur source. When used for the catalytic cracking of hydrocarbons, the contacted cracking catalyst exhibits improved resistance to the adverse effects caused by contaminants becoming deposited thereon from the feedstock. When the catalyst has deposits of contaminants thereon at the time of contact in accordance with the invention, its activity and selectivity are improved and its value for catalytic cracking immediately enhanced. Even cracking catalysts exhibiting such poor cracking behavior due to deposits thereon of contaminants that their continued use for cracking would be economically unjustifiable can be contacted in accordance with the invention and frequently economically employed for the cracking of hydrocarbon feedstock, especially for the cracking of heavy oils and the like.

DETAILED DESCRIPTION OF THE INVENTION

It has been found that tin in combination with phosphorus and/or sulfur is especially useful for passivating contaminants on a cracking catalyst. Such a combined treatment increases dramatically the selectivity of the cracking catalyst for production of a gasoline fraction. It was further found that treatment of a cracking catalyst having metals deposited thereon from the hydrocarbon feedstock with tin alone decreased catalyst activity, although this decrease in catalyst activity could be offset by employing antimony in combination with tin. It has now been found, surprisingly, that treatment of the cracking catalyst with sulfur and/or phosphorus in addition to treatment with tin can actually increase catalyst activity, increase dramatically the selectivity of the cracking catalyst for the production of gasoline range products, in addition to decreasing hydrogen and coke production, even in the absence of antimony.

The tin source of this invention is any tin composition which can be contacted with the cracking catalyst to increase the concentration of tin on the catalyst. The valence state of the tin in the composition contacted with cracking catalyst is unimportant. Thus, stannous or stannic compounds, alone or in conjunction, can be employed in the process of the present invention. Elemental tin, inorganic tin compounds and organic tin compounds as well as mixtures thereof are suitable sources of tin.

Examples of inorganic tin sources which can be employed include the elemental forms of tin: gray tin, white tin and brittle tin. Tin (II) and/or tin (IV) oxides and the hydrates of such compounds are also exemplary tin sources. Tin (II) or tin (IV) halides for example stannous fluoride, stannic fluoride, stannous chloride, stannic chloride, stannous bromide, stannic bromide, stannous iodide, stannic iodide, and tin heterohalides, for example stannic bromotrichloride as well as the hydrates of such compounds can be employed as the tin source. Stannic hydride can be used as a source of tin. Tin nitrates which can be used in accordance with the invention include stannous nitrate and stannic nitrate.

Tin selenides and tin tellurides can also be employed as the tin source.

The source of phosphorus employed in this invention can vary widely and can be any phosphorus composition which will enhance the passivation qualities of tin, or the promotion quality of sulfur for enhancing the passivating qualities of tin. Exemplary inorganic sources of phosphorus usefully employed in accordance with the invention include the white, red, violet and yellow forms of elemental phosphorus. Phosphorus halides for example phosphorus fluoride, phosphorus chloride, phosphorus bromide, phosphorus iodide and heterohalides such as phosphorus dibromotrichloride can also be usefully employed. Nitrogen containing inorganic phosphorus compounds such as phosphorus dichloronitride and phosphorus cyanide can also be used as the phosphorus source. Phosphine is also suitable for use. Exemplary of suitable phosphorus oxides which can be used in accordance with the invention are phosphorus trioxide, phosporus tetraoxide, phosphorus pentaoxide, and phosphorus sesquioxide. Oxygen containing phosphorus compounds for example phosphorus oxychloride, phosphorus oxybromide, phosphorus oxybromide dichloride, phosphorus oxyfluoride, and phosphorus oxynitride can also be used in accordance with the invention. Phosphorus selenides and phosphorus tellurides can also be used in accordance with the invention. Exemplary of this class of compounds are phosphorus triselenide and phosphorus pentaselenide. Exemplary of suitable phosphorus acids which can be used in accordance with the invention are hypophosphorus acid, metaphosphorus acid, orthophosphorus acid, and pyrophosphorus acid.

The source of sulfur employed in this invention also can vary widely and can be any sulfur composition which will enhance the passivation qualities of tin or the promotion quality of phosphorus for enhancing the passivation qualities of tin. Exemplary inorganic sources for sulfur include the alpha, beta and gamma forms of elemental sulfur. Sulfur halides such as sulfur monofluoride, sulfur tetrafluoride, disulfur decafluoride, sulfur monochloride, sulfur dichloride, sulfur tetrachloride, sulfur monobromide and sulfur iodide can also be used. Nitrogen containing sulfur compounds, for example, tetrasulfur dinitride, tetrasulfur tetranitride, and trithiazylchloride can also be used in accordance with the invention. Oxides of sulfur, for example sulfur dioxide, sulfur heptoxide, sulfur monoxide, sulfur sequioxide, sulfur tetraoxide, sulfur trioxide, trisulfur dinitrogen dioxide, sulfur monooxytetrachloride, and sulfur trioxytetrachloride are also suitable for use. The sulfur source can also be selected from sulfuric acids, for example, permonosulfuric acid, per(di)sulfuric acid and pyrosulfuric acid. Sulfurous acid is also suitable for use. Sulfuryl chlorides, for example sulfuryl chloride fluoride and pyrosulfuryl chloride are also suitable for use.

Of course, single compositions containing more than one of tin, phosphorus or sulfur can be employed as a combined source. Thus, suitable treating agents include inorganic compounds containing tin and phosphorus. Tin (II) metaphosphate, tin (II) orthophosphate, tin (II) monohydrogen orthophosphate, tin (II) dihydrogen orthophosphate, and tin (II) pyrophosphate are suitably employed. The tin phosphides are also suitable sources of tin and phosphorus. For example, tin monophosphide, tin triphosphide, and tetratintriphosphide can be used in accordance with the invention.

Likewise, inorganic compositions which contain tin and sulfur can be usefully employed as treating agents in accordance with the present invention as a combined tin-sulfur course. Exemplary of these compositions are tin (II) sulfate, tin (IV) sulfate, tin (II) sulfide, and tin (IV) sulfide.

Similarly, treating agents comprising both phosphorus and sulfur include phosphorus oxysulfide, tetraphosphorus heptasulfide, phosphoruspentasulfide, and tetraphosphorus trisulfide.

Preferably, the tin source and the at least one phosphorus source or sulfur source contain no nickel, no vanadium and no iron. Of the inorganic sources, those containing halogens are less preferred, because of their corrosive effect on process equipment. The presently preferred combination of inorganic sources are stannous oxide and phosphorus pentasulfide.

Of course, organic treating agents can be employed as the source for tin and at least one of phosphorus and sulfur. Generally, the organic treating agents contain from about one to about 48 carbon atoms for reasons of economics and availability, although organic compounds having a greater number of carbon atoms are also applicable. Thus, organic polymers can be employed. In addition to carbon and hydrogen, the organic moiety can also contain elements for example tin, phosphorus, sulfur, oxygen, nitrogen and halogen.

Examples of organic sources of tin include tin carboxylates, tin carbonates, hydrocarbyl tin compounds, and hydrocarbyl tin oxides. Thus, stannous formate, stannous acetate, stannous butyrate, stannous octoate, stannous decanoate, stannous oxylate, stannous benzoate, stannous cyclohexanecarboxylate, stannous propylcarbonate, tetrabutyltin, tetraoctyltin, tetradodecyltin, tetraphenyl tin, dipropyltin oxide, dibutyltin oxide, dioctyltin oxide, diphenyl tin oxide, stannous diethyl carbamate, tri-n-propyltin chloride and dibutyltin dibromide are suitably employed as treating agents in accordance with the present invention.

Examples of organic phosphorus sources include hydrocarbylphosphines, hydrocarbylphosphine oxides, hydrocarbylphosphites and hydrocarbylphosphates. Exemplary compounds include tri-n-butylphosphine, triphenylphosphine, tri-n-butylphosphine oxide, triphenylphosphine oxide, trioctylphosphite and triphenylphosphite.

Examples of organic sulfur sources include mercaptans, thioethers, disulfides, polysulfides, thioacids, heterocyclic sulfur compounds, and polynuclear compounds, to name but a few. Exemplary compounds include tertiary octyl mercaptan, n-butyl sulfide, tertiary amyl disulfide, tertiary butyl polysulfide, dithioacetic acid, thiophene, methyl thiophene, butylthiophene, benzothiophene, dibenzothiophene, and carbon disulfide.

Of course, compositions containing both tin and phosphorus can be employed as treating agents. Exemplary of these compounds are the tin-hydrocarbyl phosphites and tin-hydrocarbyl phosphates, for example stannous diphenylphosphite and stannous dipropylphosphate. In the preferred organic tin-phosphorus combined sources, at least one phosphorus atom is located gamma or closer to the tin. Phrased another way, the phosphorus is alpha, beta or gamma to the tin. In this embodiment, there are no more than two intervening atoms between the tin and at least one of the phosphorus atoms. Of course, more than one phosphorus atom can have this relationship with the tin.

Likewise, compositions containing tin and sulfur can be employed as a treating agent. Representative of these tin and sulfur treating agents are tin thiocarboxylates, hydrocarbyl tin mercaptoalkanoates, tin thiocarbonates, hydrocarbyltin hydrocarbyl mercaptides, and tin thiocarbamates. Examples include stannousthioacetate, stannous dithioacetate, dibutyltin bis(isooctyl mercaptoacetate), dipropyltin bis(butyl mercaptoacetate), stannous O-ethyl dithiocarbonate, dibutyltin bis(dodecyl mercaptide), stannous thiophenoxide, stannous benzene sulfonate, stannous p-toluene sulfonate, stannous propylthiocarbamate and stannous diethyl dithiocarbamate. Preferably, at least one sulfur atom in these compositions is located gamma or closer to the tin atom. In this embodiment, there are no more than two intervening atoms intermediate the tin and at least one of the sulfur atoms. At least one sulfur atom is alpha, beta or gamma to the tin. The compositions can contain more than one sulfur atom which bears this relationship to the tin.

The preferred compositions employed in this invention contain a tin source, a phosphorus source, and a sulfur source. Although any compositions containing tin, phoshorus and sulfur can be employed, it is more preferable that the composition have at least one phosphorus atom and at least one sulfur atom located at the gamm position or closer to the tin. Phrased another way, these compositions have at least one sulfur atom which is alpha, beta or gamma to tin, and at least one phosphorus atom which is alpha, beta or gamma from tin. More preferably, the sulfur and phosphorus bear this relationship to the same tin atom. Of these, the tin salts of dihydrocarbyl thiophosphoric acids are particularly preferred, because they have been tested with good results. These treating agents are conveniently represented by the formula

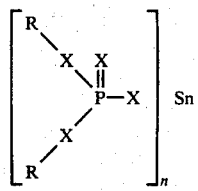

wherein the R groups can be the same or different and each comprise hydrocarbyl radicals having from 1 to about 24 carbon atoms, wherein the X groups are selected from the group consisting of oxygen and sulfur, and at least one of the X groups is sulfur, and where n is 2 or 4. The overall number of carbon atoms per molecule can range from 4 to about 200. The most preferred tin compounds of this class are those of the above formula wherein the R groups are alkyl radicals having from about 2 to about 10 carbon atoms per radical, for example, n-propyl, because it has been tested with good results. The R groups can also comprise substituted or unsubstituted $C_5$ or $C_6$ cycloalkyl radicals and substituted or unsubstituted phenyl radicals. Examples of suitable R radicals are ethyl, n-propyl, isopropyl, n-, iso-, sec- and tert-butyl, amyl, n-hexyl, isohexyl, sec-hexyl, n-heptyl, n-octyl, isooctyl, tert-octyl, dodecyl, octyldecyl, cyclopentyl, methylcyclopentyl, cyclohexyl, methylcyclohexyl, ethylcyclohexyl, phenyltoluyl, cresol, ethylphenyl, butylphenyl, amylphenyl, octylphenyl, vinylphenyl, and the like. Preferably, the hydrocarbyl radicals are bonded to phosphorus through an oxygen atom, because such compounds can be prepared by reacting an alcohol, such as n-propanol, with phosphorus pentasulfide to produce a O,O-dihydrocarbyl-phosporodithioic acid and reacting this acid or a salt thereof with a suitable tin compound to produce the tin salt. These compounds are conveniently represented by the formula

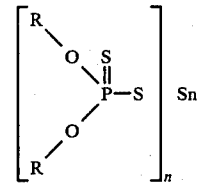

wherein R and n are as defined before.

These treating agents are most preferred because they are very effective passivating agents, are simple and inexpensive to prepare, and, because of their oil solubility, are well adapted to dissolve in hydrocarbon feedstock and meter continuously into a cyclic cracking process. Examples of the most preferred treating agents are: stannous O,O-diethyl dithiophosphate; stannic O,O-diethyl dithiophosphate; stannous O,O-di-n-propyl dithiophosphate; stannic O,O-di-n-propyl dithiophosphate; stannous O,O-diisopropyl dithiophosphate; stannic O,O-diisopropyl dithiophosphate; stannous O,O-di-n-butyl dithiophosphate; stannic O,O-di-n-butyl dithiophosphate; stannous diisobutyl dithiophosphate; stannic O,O-diisobutyl dithiophosphate; stannous O,O-di-sec-butyl dithiophosphate; stannic O,O-di-sec-butyl dithiophosphate; stannous O,O-di-tert-butyl dithiophosphate; stannic O,O-di-tert-butyl dithiophosphate; stannous O,O-diamyl dithiophosphate; stannic O,O-diamyl dithiophosphate; stannous O,O-di-n-hexyl dithiophosphate; stannic O,O-di-n-hexyl dithiophosphate; stannous O,O-di-sec-hexyl dithiophosphate; stannic O,O-di-sec-hexyl dithiophosphate; stannous O,O-di-n-heptyl dithiophosphate; stannic O,O-di-n-heptyl dithiophosphate; stannous O,O-di-n-octyl dithiophosphate; stannic O,O-di-n-octyl dithiophosphate; stannous O,O-diisooctyl dithiophosphate; stannic O,O-diisooctyl dithiophosphate; stannous di-tert-octyl dithiophosphate; stannic O,O-di-tert-octyl dithiophosphate; stannous O,O-didodecyl dithiophosphate; stannic O,O-didodecyl dithiophosphate; stannous O,O-dioctyldecyl dithiophosphate; stannic O,O-dioctyldecyl dithiophosphate; stannous O,O-dicyclopentyl dithiophosphate; stannic O,O-dicyclopentyl dithiophosphate; stannous O,O-dimethylcyclopentyl dithiophosphate; stannic O,O-dimethylcyclopentyl dithiophosphate; stannous O,O-dicyclohexyl dithiophosphate; stannic O,O-dicyclohexyl dithiophosphate; stannous O,O-dimethylcyclohexyl dithiophosphate; stannic O,O-dimethylcyclohexyl dithiophosphate; stannous O,O-diethylcyclohexyl dithiophosphate; stannic O,O-diethylcyclohexyl dithiophosphate; stannous O,O-diphenyltoluyl dithiophosphate; stannic O,O-diphenyltoluyl dithiophosphate; stannous O,O-dicresol dithiophosphate; stannic O,O-dicresol dithiophosphate; stannous O,O-diethylphenyl dithiophosphate; stannic O,O-diethylphenyl dithiophosphate; stannous O,O-dibutylphenyl dithiophosphate; stannic O,O-dibutylphenyl dithiophosphate; stannous O,O-diamylphenyl dithiophosphate; stannic O,O-diamylphenyl dithiophosphate; stannous O,O-dioctylphenyl dithiophosphate; stannic O,O-dioctylphenyl dithiophosphate; stannous O,O-divinylphenyl dithiophosphate; and stannic O,O-divinylphenyl dithiophosphate.

Of these compounds, stannous O,O-di-n-propyl phosphorodithioate and stannic O,O-di-n-propylphosphorodithioate are most preferred, because they have been tested with good results and are relatively stable.

The tin/phosphorus and tin/sulfur ratios in these compositions can be varied by utilizing stannic or stannous salts of the dihydrocarbyl thiophosphoric acids. For example, tin (IV) O,O-di-n-propyl phosphorodithioates can be prepared by reacting a suitable stannic compound, for example, stannic chloride, and the O,O-di-n-propyl dithiophosphoric acid or, more preferably, a suitable salt thereof, for example potassium dipropyl dithiophosphate, in a suitable solvent, for example, tetrahydrofuran. Tin (II) O,O-di-n-propyl phosphorodithioates can be prepared by a double decomposition reaction between a tin (II) carboxylate, for example, tin (II) octanoate and the thiophosphoric acid, for example, with O,O-di-n-propylphosphorodithioic acid dissolved in cyclohexane. The tin salt thus produced can be used effectively to treat metals contaminated fluid catalytic cracking catalysts without removing the free carboxylic acid that it contains.

Compositions represented by the above formula can thus have a wide range of tin/phosphorus ratios, tin/sulfur ratios, and phosphorus/sulfur ratios. Treatment of cracking catalysts with tin and at least one of phosphorus and sulfur in accordance with this invention effectively reduces the detrimental effects of metals contamination on the cracking catalyst to the cracking process especially that of decreased catalyst selectivity for gasoline.

In accordance with this invention, a cracking catalyst is contacted with a passivating amount of a tin source and a promoting amount of at least one of a phosphorus source and a sulfur source. By passivating amount of tin source is meant an amount of the tin source sufficient to provide at least one improvement selected from the group consisting of an increase in catalyst activity, an increase in the selectivity of the catalyst for gasoline-range products, a reduction in the production of coke, and a reduction in the production of hydrogen. By a promoting amount of at least one of the sulfur source and phosphorus source is meant an amount of such source which provides an enhancement in said at least one improvement and/or provides at least one additional improvement, the enhancement or additional improvement being of a magnitude which is greater than the improvement which would result from contacting the cracking catalyst with at least one of the sulfur source or phosphorus source in a like amount without contacting the cracking catalyst with the passivating amount of the tin source. Preferably, the cracking catalyst is contacted with a sufficient amount of at least one of the phosphorus source or sulfur source in addition to the tin source to provide an increase in the selectivity of the cracking catalyst for cracking the feedstock to gasoline range products.

Generally, the cracking catalyst is contacted with a sufficient amount of tin to impart to the cracking catalyst a tin concentration of between about 0.0001 through 4 percent by weight tin based on the weight of the tin-treated cracking catalyst. More often, the cracking catalyst is contacted with a sufficient amount of tin to impart thereto from about 0.001 to about 2 weight percent tin based on the weight of the tin-treated cracking catalyst. A tin concentration on the cracking catalyst of from about 0.005 to 1 percent by weight tin based on the weight of the tin-treated cracking catalyst is a more preferred amount of tin for reasons of economy, with a tin concentration of from 0.01 to 0.15 weight percent based on weight of tin-treated cracking catalyst being the most preferred because it closely encompasses tin concentrations which have been tested with good results. In addition to the above-described amounts of tin, the cracking catalyst is contacted with a sufficient amount of at least one of phosphorus or sulfur to promote the passivating effects of the tin. When employing sulfur as the promoting agent, it is desirable to contact the cracking catalyst with from about one-half to about 8 parts by weight sulfur from the sulfur source for each part by weight of tin which has been contacted with the cracking catalyst from the tin source. When employing phosphorus as the promoting agent, it is desirable to contact the cracking catalyst with from about one-quarter to about 1 part by weight phosphorus from the phosphorus source for each part by weight tin with which the cracking catalyst has been contacted. These ratios are not exact, being based on the approximation that phosphorus or sulfur has about one-quarter of the atomic weight of tin. Preferably, the cracking catalyst is contacted with the tin source and at least one of the promoting sources simultaneously, by employing a composition and/or mixture which contains tin and at least one of sulfur and phosphorus. More preferably, the cracking catalyst is contacted with a composition which contains tin and at least one of phosphorus and sulfur. In this embodiment, the phosphorus and/or sulfur are located at positions gamma or closer, for example, alpha, beta or gamma, to the tin atom. Most preferably, the composition contains both phosphorus and sulfur both located gamma or closer to the tin atom. Normally, these compositions will contain one part by weight or less of phosphorus and from about 1 to about 4 parts by weight sulfur for each part by weight tin.

Treatment of the cracking catalyst with tin and at least one promoting source selected from sulfur-containing compositions and phosphorus-containing compositions is effective to reduce the detrimental effects of metals contamination on a cracking catalyst. The treated composition can be employed directly for catalytic cracking without first subjecting it to a heat treatment. Treatment of the cracking catalyst in accordance with this invention is also effective to reduce the susceptibility of new cracking catalyst to becoming adversely affected by deposits of contaminants from the feedstock.

When employing the present invention to reactivate used cracking catalysts, it is desirable to maintain a ratio of tin to contaminants on the catalysts from about 0.2 to 100 to about 200:100, expressed as the weight ratio of elemental tin to the combined weights of vanadium and four times the weight of nickel on the catalyst. The combined weights of vanadium and four times the weight of nickel on the cracking catalyst is commonly referred to as the vanadium equivalent and as used herein, is expressed in parts vanadium and 4 times nickel combined per million parts weight cracking catalyst including vanadium and nickel (ppm). A preferred ratio of tin to vanadium equivalents on the cracking catalyst is from about 0.5:100 to about 50:100, because ratios within such a range have been tested with good results.

A variety of methods can be used to contact the cracking catalyst with the tin source and the at least one promoting source selected from phosphorus and sulfur.

When contacting the cracking catalyst with solid compositions, the composition in finely divided form can be mixed with the cracking catalyst in an ordinary manner such as by rolling, shaking, stirring or the like. Alternatively, these sources can be dissolved or dispersed in a suitable liquid, for example, water, hydrocarbon or aqueous acid, depending in part upon the particular composition being employed, and the resulting solution or dispersant can be used to impregnate the cracking catalyst, followed by volatilization of the liquid, or the source can be precipitated onto the catalyst from a solution of the source followed by solvent removal, or, the source can be sprayed onto the catalyst. The order in which the tin source and the promoting source are contacted with the cracking catalyst is not critical. For convenience, however, it is preferred that the contacting be effected simultaneously. When employing an oil-soluble source, the preferable method for contacting the tin source and the promoting source with the cracking catalyst is to dissolve or disperse the selected sources in the hydrocarbon feedstock to be used in the cracking process. In this case, the hydrocarbon feedstock and the tin source and promoting source contact the cracking catalyst about the same time. Additionally, if desired, the cracking catalyst can be exposed to the source in vapor form to deposit the source on the catalyst. Of course, combinations of the various methods can be employed to achieve modification of the cracking catalyst with the tin source and the promoting source.

The tin source and promoting source can be contacted with used cracking catalyst, unused cracking catalyst, or mixture thereof in accordance with the present invention and prior to, and/or during the use of the catalyst. Treatment of used cracking catalyst with the tin source and promoting source increases catalyst selectivity for gasoline production, decreases the production of hydrogen and the production of coke often without harming catalyst activity. Treatment of new cracking catalysts with the tin source and promoting source aids in maintaining high catalyst selectivity for gasoline production and low hydrogen and coke production. The term "cracking catalyst" as used herein refers to either new or used cracking catalyst materials which are useful for cracking hydrocarbons in the absence of added hydrogen.

Cracking catalysts suitable for treatment in accordance with this invention can be any of those cracking catalysts employed in the catalytic cracking of hydrocarbons boiling above 400° F. (204° C.) in the absence of added hydrogen for the production of gasoline, motor fuel blending components and light distillates. Because of the high activity and selectivity of zeolite containing cracking catalysts, zeolite containing cracking catalysts are preferred. The zeolitic materials can be naturally occurring or snythetic. Generally they will have been at least partially ion exchanged with ammonium or rare earth cations. Zeolite-modified silica-alumina catalysts are particularly well suited for treatment in accordance with this invention, especially such catalysts comprising from 1 to about 50 percent by weight of zeolitic materials. Examples of cracking catalysts useful in the present invention include, for example, hydrocarbon cracking catalysts obtained by admixing an inorganic oxide gel with an aluminosilicate, and aluminosilicate compositions which are strongly acidic as the result of treatment with a fluid medium containing at least one rare earth metal cation and a hydrogen ion, or ion capable of conversion to a hydrogen ion. The catalytic cracking materials can vary in pore volume and surface area. Generally, the unused cracking catalyst will have a pore volume in the range of from about 0.1 to about 1 ml/gm. The surface area of this unused catalytic cracking material generally will be in the range of from about 50 to about 500 m$^2$/gm. The unused catalytic cracking material employed will generally be in particulate form having a particle size principally within the range of from about 10 to about 200 micrometers.

Feedstocks amenable to conversion by the treated cracking catalyst of this invention are generally oils having an initial boiling point have 204° C. This includes gas oils, fuel oils, topped crude, shale oil, waste polymers in solvent and oils from coal and/or tar sands. The feedstocks can and usually do contain significant concentrations of at least one metal selected from the group of nickel, vanadium and iron. The presence of such metals normally adversely affects catalyst selectivity and activity. Since these metals become concentrated in the least volatile fractions of oil suitable for use as feedstock, cracking the heavy oil fractions is probably the most important application for the treated cracking catalyst of this invention. Such feedstocks can contain, for example, nickel concentrations of about 100 parts per million, vanadium concentrations of about 500 parts per million, and iron concentrations of about 500 parts per million. Because nickel has a stronger affect on the activity and selectivity of the cracking catalyst than vanadium and/or iron, it is convenient to refer to the total contaminants in the feedstock in terms of parts per million by weight of total effective metals, as used herein the term "total effective metals" means the sum of vanadium, iron and four times the weight of nickel in one million parts by weight of feedstock (ppm).

Most known commercial heavy oil cracking processes are capable of cracking heavy oils having a metals content of up to about 100 ppm of total effective metals as defined above. Economically marginal results are obtained with oils having 50 to 100 parts per million of total effective metals. In accordance with this invention, heavy oils with a total metals content of about 50 to 100 ppm and even those of about 100 to 200 ppm and above of total metals can be cracked in a cracking process by utilizing the treated cracking catalyst defined above to yield gasoline and other fuels and fuel blending components. Thus, heavy oils with total metals content from about 100 to 300 ppm that could not be directly used for fuel production in most known processes and in particular for gasoline or higher boiling hydrocarbon fuels production, in accordance with this invention can be cracked to yield gasoline and higher boiling hydrocarbon fuels such as kerosene, diesel fuel and burning oils.

It is preferable to meter the tin source and at least one promoting source into the catalytic cracker along with feedstock at at least a rate which is related to the amounts of contaminants in the feedstock as set forth below.

| Total Effective Metals in Feedstock (ppm)[1] | Tin Concentration in Feedstock (ppm) |
|---|---|
| <1–40 | 0.005–20 |
| 40–100 | 0.2–50 |
| 100–200 | 0.5–100 |
| 200–300 | 1.0–200 |

| Total Effective Metals in Feedstock (ppm)[1] | Tin Concentration in Feedstock (ppm) |
|---|---|
| 300–800 | 2.0–500 |

[1]Fe(ppm) + V(ppm) + 4 Ni(ppm) by weight.

Of course, higher rates can be used if desired, for example, when it is desired to increase the concentration of tin on the cracking catalyst.

A preferred embodiment of the cracking process of the present invention utilizes cyclic flow of catalyst from a cracking zone to a regeneration zone. In this process, the hydrocarbon feedstock is contacted with a fluidized cracking catalyst in a cracking zone under cracking conditions in the absence of added hydrogen; a cracked product is obtained and recovered; the cracking catalyst is passed from the cracking zone into a regeneration zone; and in the regeneration zone the cracking catalyst is regenerated by being contacted with a free oxygen-containing gas, preferably air. The coke that has built up during the cracking process is thereby at least partially burned off the catalyst. The regenerated cracking catalyst is reintroduced into the cracking zone usually after being supplemented with a make-up catalyst.

Such cyclic catalytic cracking processes are well known to those skilled in the art. Generally, the cracking reaction takes place in the presence of fluidized cracking catalyst at catalytic cracking temperatures, for example, temperatures beteeen about 900° and 1100° F. (482° to 593° C.) usually between 940° and 1020° F. (504° to 549° C.) at catalytic cracking pressures, for example, pressures between about 5 and 50 psig (138–448 kPa) usually 15 to 35 psig (207–345 kPa). Usually, the cracking catalyst employed contains zeolitic materials. The catalyst-to-feedstock contact time is generally between about 1 and 4 seconds, and is conducted with catalyst-to-feedstock weight ratios of between about 4:1 and 15:1. Regeneration is carried out under catalyst regeneration conditions, for example, in the presence of oxygen containing gas at temperatures between 800° and 1600° F. (427° to 871° C.), usually from about 1150° to 1350° F. (621° to 732° C.) for a period of time ranging from about 3 to 30 minutes and sufficient to reduce the concentration of coke on the catalyst to less than 0.3 weight percent, preferably less than 0.1 weight percent.

In this embodiment of the invention, the tin source and one or both of the phosphorus source and the sulfur source are metered continuously into the cracking unit for contact with the cracking catalyst. The tin source and at least one of the phosphorus source and sulfur source need not be introduced into the unit at the same point. For example, at least one of the phosphorus source and sulfur source could be introduced into the cracking zone and the tin source could be introduced into the regeneration zone; or at least one promoter could be introduced into the unit at completion of regeneration into the regeneration zone, and the tin source introduced into the cracking zone. It is preferred to introduce the tin source and at least one promoter source into the cracking unit so that the tin and at least one promoter contact the cracking catalyst at about the same time. This is conveniently accomplished by mixing or dissolving the tin source and at least one promoter source into the feedstock, as previously described. When employing oil-soluble sources, the tin and at least one of phosphorus and sulfur can be diluted with a neutral hydrocarbon oil and metered into the feedstock.

The invention will be still more fully understood from the following examples, which are intended to illustrate preferred embodiments of the invention but not limit the scope thereof.

EXAMPLE 1

Synthesis of Stannic O,O-Dihydrocarbylphosphorodithioates

The subject compound is prepared by a double decomposition (or metathesis) reaction between a stannic salt and dihydrocarbylphosphorodithioic acid or, preferably, a salt of the acid with an element from Group Ia or IIa of the periodic table of the elements, such as lithium, sodium, potassium, magnesium, and calcium. In the anion of the phosphorus compound $[(RO)_2PS_2]^-$ R is a hydrocarbyl radical that contains from one to about 24 carbon atoms and can be an alkyl, cycloalkyl, alkenyl, cycloalkenyl, or aryl radical or a combination of these radicals such as alkaryl, aralkyl, etc. Examples of suitable hydrocarbyl radicals are methyl, normal and isopropyl, normal and branched hexyl, decyl, and octadecyl, cyclohexyl, cyclohexenyl, phenyl, xylyl, 1- and 2-anthracyl, and the like.

Suitable stannic salts for the double decomposition reaction are, in general, those that are soluble in the solvent selected for the reaction medium. Examples are the stannic halides, particularly the chlorides, bromides, and iodides, and stannic sulfate.

Solvents suitable to effect the synthesis of tin dihydrocarbylphosphorodithioate are those in which the reactants and the tin produce are soluble to at least a limited extent. Examples are water and polar organic compounds such as methanol and ethanol, tetrahydrofuran, acetone, and the like, and mixtures thereof. Reaction conditions for the synthesis are not critical. Temperature for the reaction can range generally from 0° C. to 75° C.; for convenience of operation ambient temperatures are preferred. The reaction appears to resemble ionic reactions in its speed. Consequently extended reaction times are not required although a time of 2–3 hours can be used at the lower limits of the cited temperature range. At about 25° C. and above the reaction can be considered to be complete when the reactants have been combined but additional time can be used to permit phase separation of the products, e.g., oils from aqueous solution or inorganic salts from organic solvents. The order in which reactants are combined is not critical, i.e., the tin salt can be added to the phosphorus-containing reactant or vice versa. And, since the reaction is not equilibrium limited the preferred ratio for combining reactants is the stoichiometric. (This does not imply quantitative yields because nonproductive reactions can occur, e.g., the tin compound with the solvent). Although the quantity of solvent in which the reaction occurs is not critical, it will conveniently be at least about one liter per gram-mole of total reactants. Preferably there will be sufficient solvent to dissolve completely the reactants.

For many purposes, including the preparation of a passivating agent for metals-contaminated cracking catalyst, it is required to separate the desired product from the by-product of the double decomposition reaction. When water is the solvent this can be done conveniently by separating the product which appears as an insoluble oil. When any of the organic solvents cited above are used, the resulting inorganic salt is precipitated and can be separated by filtration, centrifugation, etc.

The following illustrates the synthesis of tin (IV) di-n-propylphosphorodithioate:

To a solution of 3.51 g (grams) (10 mmol) of $SnCl_4.5H_2O$ in about 50 mL (milliters) of tetrahydrofuran (THF) was added dropwise a solution of 10.10 g (40 mmol) of potassium di-n-propylphosphorodithioate in about 50 mL of THF. The solution immediately became bright yellow and potassium chloride precipitated. The mixture was warmed to 65° C. for 30 minutes, cooled to room temperature, and filtered to remove the potassium chloride. THF was removed from the filtrate with a rotary evaporator and the residue was treated with about 50 mL of n-hexane; this solution was again filtered to remove unconverted reactants and finally n-hexane was removed from the product with a rotary evaporator. Yield of product was 7.15 g, which was 74% of the calculated theoretical yield. Elemental analyses on the product, calculated as $C_{24}H_{56}O_8P_4S_8Sn$, were: calculated 29.66% C, 5.81% H, 12.75% P, and 12.21% Sn; found 29.00% C, 5.63% H, 12.2% P, and 11.7% Sn.

EXAMPLE II

Synthesis of Stannous Bis(di-n-propylphosphorodithioate)

A solution of 25 g. (0.048 moles) of stannous octanoate (Catalyst T-9 from M & T Chemicals Inc., Rahway, N.J.) in about 25 mL of cyclohexane was treated dropwise, at about 25° C., with 20.76 g. (0.097 moles) of $(C_3H_7O)_2PS_2H$, with constant stirring. The solution became orange-brown immediately and was deep mahogany when addition was complete. After standing for three days the solvent was removed from the preparation with a rotary evaporator, leaving a viscous liquid product. Upon chemical analysis it was found to contain 16.3 weight percent tin.

EXAMPLE III

Two commercial fluid cracking catalysts comprising amorphous silica-alumina and rare earth cation-exchanged zeolite, were used in a commercial fluid catalytic cracker until they had attained equilibrium with respect to metals accumulation (catalyst was being removed from the process systems at a constant rate) and were characterized by the following properties:

TABLE I

| CATALYST I | |
|---|---|
| Surface area, m²/g (square meters per gram) | 74.3 |
| Pore Volume, mL/g (milliliters per gram) | 0.29 |
| Composition, wt. % | |
| Aluminum | 21.7 |
| Silicon | 24.6 |
| Sodium | 0.39 |
| Cerium | 0.40 |
| Carbon | 0.06 |
| Nickel | 0.38 |
| Vanadium | 0.60 |
| Iron | 0.90 |

Catalyst I contained 21,200 ppm vanadium equivalents.

TABLE II

| CATALYSTS II | |
|---|---|
| Surface area, m²/g | 89.2 |
| Pore Volume, mL/g | 0.30 |
| Composition, wt. % | |
| Aluminum | 19.7 |
| Silicon | 26.5 |
| Sodium | 0.49 |
| Cerium | 0.60 |
| Carbon | 0.17 |
| Nickel | 0.038 |
| Vanadium | 0.11 |
| Iron | 0.62 |

Catalyst II contained about 2620 ppm vanadium equivalents.

A topped crude oil from Borger, Tex. is characterized by the following properties:

TABLE III

| Feed I | |
|---|---|
| API gravity at 60° F. | 21.3 |
| Carbon residue, Conradson | 5.33 wt. % |
| Elemental analysis | |
| Sulfur | 1.9 wt. % |
| Nitrogen | 0.28 wt. % |
| Sodium | 0.5 ppm |
| Nickel | 5.24 ppm |
| Vanadium | 14.2 ppm |
| Iron | 7.4 ppm |

A gas oil from Sweeny, Tex. is characterized by the following properties:

TABLE IV

| Feed II | |
|---|---|
| API gravity at 60° F. | 25.8 |
| Carbon residue, Ramsbottom | 0.87 wt. % |
| Elemental analysis | |
| Sulfur | 0.40 wt. % |
| Nitrogen | 0.07 wt. % |

A gas oil from Kansas City is characterized by the following properties

TABLE V

| Feed III | |
|---|---|
| API gravity at 60° F. | 30.2 |
| Carbon residue, Ramsbottom | 0.23 wt. % |
| Elemental analysis | |
| Sulfur | 0.2 wt. % |
| Nitrogen | 0.08 wt. % |
| Nickel | 0.25 ppm |
| Vanadium | 9 ppm |

EXAMPLE IV

Catalyst I was employed to crack Feed I in a laboratory-sized fluidized bed quartz reactor at 510° C. and atmospheric pressure with about 0.5 minute cracking periods and about 30 minutes intervening regeneration periods at about 649° C. The runs were carried out at a number of different catalyst/oil ratios and the data presented in Table VI were from regression analysis curves calculated from the observed data points. In this and subsequent examples, treatment of experimental data by regression analysis is based on not less than five runs; generally the analysis utilized at least 10 runs.

The data are presented to show the cracking behavior of metals contaminated fluid catalytic cracking catalyst at varying conversion levels. Conversion is increased by increasing the catalyst/oil ratio, for example, by reducing the oil feed rate. Note that as conversion increases, the selectivity of the cracking catalyst for gasoline production declines, even though the yield of gasoline increases. Coke and hydrogen production also increase at increasing levels of conversion.

Catalyst I was also employed to crack Feed II at varying levels of conversion. Results from regression analysis of these runs are presented in Table VII.

A comparison of the data set forth in Table VI to that set forth in Table VII shows that the activity of the cracking catalyst to crack Feed I is greater than its activity to crack Feed II. However, the trends shown by Table VII are in the same directions as those in Table VI. As conversion levels increase, the selectivity of the cracking catalyst to convert the feed to gasoline products decreases and the absolute yield of gasoline, coke and hydrogen all increase.

EXAMPLE V

Four samples of catalyst I were treated to contain varying concentrations of dibutyltin oxide. This was done by combining weighed portions of dry catalyst with weighed portions of dibutyltin oxide that had been ground to pass a 325 mesh sieve. These components were mixed by shaking, then were conditioned in the following manner. The catalyst was placed in a laboratory-sized confined fluid bed quartz reactor and heated from room temperatures (about 20° C.) to about 482° C. while fluidized with nitrogen, then treated from that temperature to about 650° C. while fluidized with hydrogen. While maintained at 650° C. the catalyst was fluidized for 5 minutes with nitrogen followed by fluidization for 15 minutes with air. The catalyst was then aged by being subjected to 10 cycles, each cycle consisting of the following treatment. The catalyst was cooled from 650° C. for 30 seconds while fluidizing with air, then cooled to about 482° C., fluidized with nitrogen for one minute, then heated to about 650° C. during two minutes while fluidized with hydrogen, then maintained at about 650° C. for one minute while fluidized with nitrogen, then maintained at 650° C. for 10 minutes while fluidized with air, and then cooled to about 482° C. during about 0.5 minutes while fluidization with air continued. After 10 such cycles the catalyst was used in runs conducted as described in Example IV. The tin content of five catalysts together with results of runs made to crack Feed II at a catalyst/oil ratio of 7.7 are presented in Table VIII.

Table IX presents results from these catalysts obtained at 64% conversion; these were obtained from regression analysis curves derived from a large number of runs with these catalysts.

As is apparent from the Conversion column of Table VIII, impregnation of the cracking catalyst with dibutyltin oxide to any of the tin concentrations indicated decreased the cracking ability of the cracking catalyst. As shown by the Selectivity to Gasoline column of Table IX, impregnation of the cracking catalysts with dibutyltin oxide somewhat increased the selectivity of the cracking catalyst for gasoline production. In particular note that impregnation of the cracking catalyst to 0.1 wt. % Sn increased the selectivity of the cracking catalyst for gasoline production by only about 1% at constant conversion of 64 vol. %.

The results are summarized in Tables VIII and IX.

EXAMPLE VI

Six samples of catalyst I were treated to contain varying concentrations of tributyl phosphine by impregnating weighed portions with a solution of tributyl phosphine in dry cyclohexane. After removal of solvent by evaporation, the catalysts were used in runs to crack Feed III. These runs were made in a fixed bed reactor at 482° C. The catalyst/oil ratio was adjusted to obtain 75 volume percent conversion of the feed.

The selectivity to gasoline, the coke content and the hydrogen production were measured. All results were compared relative to the results obtained with a catalyst containing no treating agent which were arbitrarily given a rating of 1.00. The selectivity to gasoline is defined as the volume of liquid products boiling below 400° F. divided by the volume of oil converted times 100. The oil converted is the volume of feed minus the volume of recovered liquid boiling above 400° F. Thus, for instance, if the selectivity to gasoline of the untreated catalyst was 50 volume percent, the selectivity of a treated catalyst of 1.04 in the following table would refer to a selectivity of 52 volume percent of this treated catalyst.

The coke content of the catalyst is measured by weighing the dry catalyst after the cracking process. The hydrogen quantity produced is determined in standard equipment analyzing the hydrogen content of the gaseous products leaving the reactor.

The phosphorus content of these catalysts and the results of the runs are summarized in Table X.

In particular, note that impregnation of the cracking catalyst to a level of 0.1 wt. % P increased the selectivity of the cracking catalyst for gasoline production by only about 2% at constant conversion of 75 vol. %.

EXAMPLE VII

A sample of catalyst I was treated with $P_2S_5$ by combining a weighed quantity of the catalyst with a weighed portion of solid $P_2S_5$. These components were mixed by shaking. The resulting mixture was conditioned and aged as detailed in Example V, then used in a run to crack Feed I as described in Example IV. The phosphorus content of this catalyst together with results of runs made with it and with a control are presented in Table XI.

As shown by the decreased catalyst/oil ratio, the addition of $P_2S_5$ increased the activity of the cracking catalyst for cracking the hydrocarbon feed. The process increased the selectivity of the cracking catalyst for gasoline production by about 3.9% at a conversion level of 74%.

EXAMPLE VIII

A sample of Catalyst I was treated with $P_2S_5$ to a phosphorus level of 0.1 wt. % P exactly as described in Example VII. The treated cracking catalyst, after conditioning and aging, is employed in fluid catalytic cracking of Feed II at about 950° F. following the procedure described in Example IV. The results are shown in Table XII.

The above results appear to somewhat contradict those shown by Table XI. In the runs set forth in Table XII, it appears that the incorporation of $P_2S_5$ into the catalyst decreased slightly the activity of the cracking catalyst for cracking the hydrocarbon feed, and decreased the selectivity of the catalyst for gasoline production at about the same conversion level by about 7.0%.

EXAMPLE IX

A sample of Catalyst II was impregnated with a cyclohexane solution of $(C_4H_9)_2Sn(SCH_2CO_2C_8H_{17})_2$ (Thermolite 31, commercially available from M & T Chemicals, Inc.) to a tin concentration of 0.011 wt. % and employed to crack feed III. After removal of solvent the catalyst preparation was conditioned and aged as described in Example V. The catalyst, together with an untreated control, was used in runs at several catalyst/oil ratios. These are defined and results of the runs are summarized in Table XIII.

The impregnation of the cracking catalyst with Thermolite 31 to a tin level of 0.011 wt. % Sn decreased catalyst activity, increased catalyst selectivity for gasoline production, increased coke production and appeared to decrease hydrogen production at high conversion levels. At 70% conversion, the tin and sulfur treated cracking catalyst increased selectivity to gasoline by 4.5%. At 75% conversion, the improvement was 2.9%. At 80% conversion, the improvement was 1.5%. Comparison of the results set forth in Table XIII to those of Table IX shows that the tin-sulfur treatment improved catalyst selectivity for gasoline production substantially better than treatment with tin alone. In fact, on a weight basis of tin added, it would appear that treatment of the catalyst with tin and sulfur in combination is at least 10 times more effective for improving catalyst selectivity for gasoline production than treatment with tin alone. Because a commercial cracking unit often has 200 tons or more of circulating catalyst, the greater efficacy of tin and sulfur for improving catalyst selectivity for gasoline production can represent a substantial economic savings.

EXAMPLE X

A sample of Catalyst I was impregnated with stannic di-n-propyl phosphorodithioate to a tin concentration of 0.1 wt. % Sn. The weight ratio of phosphorus to tin contacted with the cracking catalyst was about 1:1. The weight ratio of sulfur to tin contacted with the cracking catalyst was about 2:1. The weight ratio of phosphorus to sulfur contacted with the cracking catalyst was about 1:2.

The treated cracking catalyst after conditioning and aging as described in Example V was employed for the fluid catalytic cracking of Feed II at 950° F. following the procedure used in Example IV. The results are set forth in Table XIV.

Treatment of the cracking catalyst with tin, phosphorus and sulfur slightly improved catalyst activity, decreased hydrogen and coke production, and increased catalyst selectivity for gasoline production at a slightly higher conversion level by about 11%. This is especially surprising in view of the data presented in Tables IX and XIII. Impregnation of the same cracking catalyst of this example with the tin compound of Example V to a level of 0.1 wt. % Sn improved catalyst selectivity for cracking the same feedstock to gasoline by only about 1%. Impregnation of the same cracking catalyst of this example with $P_2S_5$ of Example VIII to a level of 0.1 wt. % P decreased catalyst selectivity for cracking the same feedstock gasoline by about 7.0% at a conversion level of 64%. It is remarkable that the combined Sn-P-S treatment of this example provided an improvement in catalyst selectivity for gasoline production of about 11%.

EXAMPLE XI

In Example II of U.S. Pat. No. 4,101,417, a sample of zeolite-containing cracking catalyst having 10,350 vanadium equivalents deposited thereon was impregnated with hexabutyltin to a level of 0.61 wt. % Sn and another sample was impregnated with tin chloride to a tin concentration of 0.61 wt. % Sn and thereafter contaminated with 10,350 vanadium equivalents. Because of the high surface area, it does not appear that the catalyst to be treated in that patent was an equilibrium cracking catalyst. The hexabutyltin treatment increased conversion by about 7.3% and selectivity to gasoline by about 3.8% at the higher conversion level. The tin chloride treatment increased conversion by about 13.7% and selectivity to gasoline by about 4.1% at the higher conversion level. The weight ratio of tin to vanadium equivalents on the cracking catalyst was about 0.6:1. In Example X of this application, the weight ratio of tin to vanadium equivalents on the cracking catalyst was about 0.047:1. Regarding the apparent discrepancy between Example V of the present application and Example II of U.S. Pat. No. 4,101,417, it should be noted that the catalyst employed in Example V was an equilibrium cracking catalyst with metallic deposits accumulated thereon during commercial employment of the cracking catalyst, whereas fresh metals were present on the cracking catalyst employed in the examples of U.S. Pat. No. 4,101,417. It is believed that the susceptibility of metals deposited on the cracking catalyst during the cracking of metals laden feedstock to becoming passivated by treating agents is different from the susceptibility of metals freshly deposited by other means. The discovery that treatment of cracking catalysts containing equilibrium deposits of metals with tin and at least one of phosphorus and sulfur provided dramatically improved catalyst selectivity for gasoline production is especially surprising in view of the rather poor performance of tin alone on the same cracking catalyst.

EXAMPLE XII

A catalyst containing 0.10 wt. % tin was prepared by impregnating 40 g. of catalyst I with 0.325 g. of tin(IV) dipropyl phosphorodithioate in 40 mL of cyclohexane. The solvent was removed by evaporation and the dry catalyst was placed in a vertical quartz tube reactor in a tube furnace. While being fluidized with nitrogen the catalyst was heated to 482° C. Nitrogen was replaced with hydrogen and the temperature was raised to 649° C. Nitrogen replaced hydrogen and the catalyst was fluidized for 5 minutes to purge the reactor after which the catalyst was fluidized with air for 15 minutes at that temperature.

A catalyst containing 0.10 wt. % antimony and 0.01 wt. % tin was prepared by impregnating 40 g. of Catalyst I with 0.363 g. of antimony (III) dipropylphosphorodithioate and 0.033 g. of the tin compound in 40 ml of cyclohexane. The solvent was removed by evaporation and the catalyst conditioned as described above.

A catalyst containing 0.10 wt. % of antimony was prepared as described immediately above except that the addition of tin was omitted.

A sample of catalyst I and the three above described modified catalysts were employed to crack feedstock II at 510° C. in fluidized bed reactors. Atmospheric pressure was used with 0.5 minute cracking periods and intervening regeneration periods at 649° C.

Before being tested, each of the catalysts was aged by fluidization with nitrogen at about 482° C. for about one minute, then heated to 510° C. while fluidized with hydrogen for 2 minutes, then fluidized with nitrogen at 510° C. for 1 minute, then fluidized with air at about 649° C. for ten minutes, then cooled to about 482° C. under air fluidization over about 0.5 minute. After 10 such cycles, the catalysts were cooled to room temperature while being fluidized with nitrogen.

Results of the cracking runs are summarized in Table XVI.

As is apparent from the data presented in Table XVI, treatment of the cracking catalyst with tin and antimony di-n-propylphosphorodithioate to provide in the catalyst a tin:antimony weight ratio of about 1:10 synergistically improved at least the cracking activity of the cracking catalyst.

A catalyst containing 0.10 wt. % tin was prepared by dry blending dibutyltin oxide (ground until it passed through a 325 mesh screen) with a portion of Catalyst I. The blend was wetted with cyclohexane and the resulting mixture taken to apparent dryness by heating on a hot plate. The catalyst was preconditioned and aged similarly to the method described above and employed to fluid catalytically crack feedstock II as described above. A series of runs were made at varying catalyst/oil ratios and the results shown below in Table XVI are read from a smooth curve fit of the data points.

A catalyst containing 0.10 wt. % antimony and 0.01 wt. % tin was prepared by dry blending dibutyltin tin oxide with a portion of catalyst I as described above followed by impregnation with a mineral oil solution of antimony (III) dipropylphosphorodithioate dissolved in cyclohexane in place of the wetting step with cyclohexane as described above. The resulting catalyst was then conditioned and aged as described above and employed to fluid catalytically crack feedstock II as described above. A series of runs were made at varying catalyst/oil ratios and the results shown below in Table XVI are read from a smooth curve fit of the data points.

A catalyst containing 0.10 wt. % antimony was prepared as described above except that dibutyltin oxide was not first mixed with the catalyst. A series of runs were made at varying catalyst/oil ratios and the results shown below in Table XVI are read from a smooth curve fit of the data points.

Comparison of the runs in Tables XV and XVI employing antimony and tin in combination yields no clue as to the surprising effectiveness of the particular tin compound tested by itself in Table XV.

TABLE VI

| Conversion Vol. % | Selectivity to Gasoline (% vol) | Gasoline (vol. %) | Coke (wt. %) | $H_2$(SCF/bbl conv.) | Catalyst/Oil Ratio |
|---|---|---|---|---|---|
| 70 | 77.5 | 54.2 | 13.8 | 797 | 5.3 |
| 71 | 77.2 | 54.8 | 14.1 | 805 | 5.7 |
| 72 | 77.0 | 55.4 | 14.4 | 817 | 6.0 |
| 73 | 76.8 | 56.0 | 14.6 | 825 | 6.3 |
| 74 | 76.5 | 56.6 | 14.9 | 836 | 6.6 |
| 75 | 76.2 | 57.1 | 15.2 | 848 | 6.9 |
| 76 | 75.9 | 57.6 | 15.4 | 857 | 7.2 |
| 77 | 75.5 | 58.1 | 15.7 | 867 | 7.5 |
| 78 | 75.0 | 58.5 | 15.9 | 876 | 7.8 |
| 79 | 74.0 | 58.9 | 16.3 | 888 | 8.3 |
| 80 | 73.8 | 59.0 | 16.6 | 898 | 8.7 |

TABLE VII

| Conversion Vol. % | Selectivity to Gasoline (% vol) | Gasoline (vol. %) | Coke (wt. %) | $H_2$(SCF/bbl conv.) | Catalyst/Oil Ratio |
|---|---|---|---|---|---|
| 60 | 86.5 | 51.9 | 5.8 | 621 | 5.7 |
| 61 | 85.9 | 52.4 | 6.1 | 624 | 6.2 |
| 62 | 85.2 | 52.8 | 6.6 | 627 | 6.6 |
| 63 | 84.4 | 53.2 | 7.0 | 629 | 7.1 |
| 64 | 83.8 | 53.6 | 7.6 | 630 | 7.5 |
| 65 | 82.9 | 53.9 | 8.0 | 632 | 8.0 |
| 66 | 82.3 | 54.3 | 8.4 | 634 | 8.4 |
| 67 | 81.6 | 54.7 | 8.9 | 635 | 8.9 |
| 68 | 81.1 | 55.1 | 9.3 | 636 | 9.3 |
| 69 | 80.3 | 55.4 | 9.7 | 638 | 9.8 |
| 70 | 79.7 | 55.8 | 10.3 | 639 | 10.3 |

TABLE VIII

| Run No. | Additive[1] | Cat[2]/Oil[3] Ratio | Conversion (vol. %) | Selectivity to Gasoline (vol. %) | Gasoline (vol. %) | $H_2$(SCF/bbl Conv.) | Coke (wt. %) |
|---|---|---|---|---|---|---|---|
| 1 | None | 7.7 | 64 | 83.3 | 53.3 | 640 | 8.0 |
| 2 | 0.01 wt. % Sn | 7.7 | 62 | 85.0 | 52.7 | 638 | 7.8 |
| 3 | 0.1 wt. % Sn | 7.7 | 61.4 | 88.1 | 54.1 | 578 | 7.2 |
| 4 | 0.5 wt. % Sn | 7.7 | 62 | 88.1 | 54.6 | 480 | 6.6 |
| 5 | 1.0 wt. % Sn | 7.7 | 60.1 | 89.7 | 53.9 | 530 | 6.6 |

[1] dibutyltin oxide;
[2] 21,200 vanadium equivalents;
[3] 25.8° API

TABLE IX

| Run No. | Additive[1] | Cat[2]/Oil[3] Ratio | Conversion (vol. %) | Selectivity to Gasoline (vol. %) | Gasoline (vol. %) | $H_2$(SCF/bbl Conv.) | Coke (wt. %) |
|---|---|---|---|---|---|---|---|
| 1 | None | 7.8 | 64 | 83.1 | 53.2 | 640 | 8.2 |
| 2 | 0.01 wt. % Sn | 8.8 | 64 | 83.3 | 53.3 | 640 | 8.2 |
| 3 | 0.1 wt. % Sn | 8.8 | 64 | 83.9 | 53.7 | 615 | 7.8 |
| 4 | 0.5 wt. % Sn | 8.9 | 64 | 84.7 | 54.2 | 560 | 7.3 |

TABLE IX-continued

| Run No. | Additive[1] | Cat[2]/Oil[3] Ratio | Conversion (vol. %) | Selectivity to Gasoline (vol. %) | Yields Gasoline (vol. %) | H$_2$(SCF/bbl Conv.) | Coke (wt. %) |
|---|---|---|---|---|---|---|---|
| 5 | 1.0 wt. % Sn | 8.9 | 64 | 85.2 | 54.5 | 500 | 7.0 |

[1]dibutyltin oxide;
[2]21,200 vanadium equivalents;
[3]25.8° API

TABLE X

| Run No. | Additive | Cat[2]/Oil[3] Ratio | Conversion (vol. %) | Selectivity to Gasoline (vol.%) | Yields Gasoline (vol. %) | H$_2$(SCF/bbl Conv.) | Coke (wt. %) |
|---|---|---|---|---|---|---|---|
| 1 | None | — | — | 1.00 | — | 1.00 | 1.00 |
| 2 | 0.1 wt.% P | — | 75 | 1.02 | — | 0.91 | 1.00 |
| 3 | 0.2 wt.% P | — | 75 | 1.04 | — | 0.86 | 0.98 |
| 4 | 0.3 wt.% P | — | 75 | 1.05 | — | 0.82 | 0.97 |
| 5 | 0.4 wt.% P | — | 75 | 1.04 | — | 0.79 | 0.97 |
| 6 | 0.5 wt.% P | — | 75 | 1.04 | — | 0.78 | 0.96 |
| 7 | 1.0 wt.% P | — | 75 | 1.01 | — | 0.74 | 0.92 |

[1]tributyl phosphine;
[2]21,200 vanadium equivalents;
[3]30.2° API

TABLE XI

| Run No. | Additive[1] | Cat[2]/Oil[3] Ratio | Conversion (vol. %) | Selectivity to Gasoline (vol.%) | Yields Gasoline (vol. %) | H$_2$(SCF/bbl Conv.) | Coke (wt. %) |
|---|---|---|---|---|---|---|---|
| 1 | None | 6.5 | 74 | 67.3 | 49.8 | 840 | 16.4 |
| 2 | 0.085 wt. % P | 6.15 | 74 | 69.9 | 51.7 | 740 | 14.3 |

[1]$P_2S_5$;
[2]21,200 vanadium equivalents;
[3]21.3° API

TABLE XII

| Run No. | Additive[1] | Cat[2]/Oil[3] Ratio | Conversion (vol. %) | Selectivity to Gasoline (vol.%) | Yields Gasoline (vol. %) | H$_2$(SCF/bbl Conv.) | Coke (wt. %) |
|---|---|---|---|---|---|---|---|
| 1 | None | 7.8 | 64 | 83.1 | 53.2 | 640 | 8.2 |
| 2 | 0.1 wt.% P | 7.8 | 62.1 | 76.7 | 47.7 | 432 | 7.9 |
| 3 | 0.1 wt.% P | 7.6 | 65.0 | 77.9 | 50.6 | 453 | 7.8 |
| 4 | average 0.1 P | 7.7 | 63.55 | 77.3 | 49.15 | 442.5 | 7.85 |

[1]$P_2S_5$;
[2]21,200 vanadium equivalents;
[3]25.8° API

TABLE XIII

| Run No. | Additive[1] | Cat[2]/Oil[3] Ratio | Conversion (vol. %) | Selectivity to Gasoline (vol.%) | Yields Gasoline (vol. %) | H$_2$(SCF/bbl Conv.) | Coke (wt. %) |
|---|---|---|---|---|---|---|---|
| 1 | None | 4.6 | 70 | 84.6 | 59.2 | 165 | 6.4 |
| 2 | 0.011 wt. % Sn | 5.4 | 70 | 88.4 | 61.9 | 171 | 7.9 |
| 3 | None | 5.8 | 75 | 84.0 | 63.0 | 187 | 7.5 |
| 4 | 0.011 wt. % Sn | 6.4 | 75 | 86.4 | 64.8 | 180 | 8.9 |
| 5 | None | 7.2 | 80 | 82.6 | 66.1 | 209 | 8.7 |
| 6 | 0.011 wt. % Sn | 7.4 | 80 | 83.8 | 67.0 | 188 | 9.9 |

[1]$(C_4H_9)_2Sn(SCH_2CO_2C_8H_{17})_2$;
[2]2,620 vanadium equivalents;
[3]30.2° API

TABLE XIV

| Run No. | Additive[1] | Cat[2]/Oil[3] Ratio | Conversion (vol. %) | Selectivity to Gasoline (vol.%) | Yields Gasoline (vol. %) | H$_2$(SCF/bbl Conv.) | Coke (wt. %) |
|---|---|---|---|---|---|---|---|
| 1 | None | 7.7 | 64.5 | 80.2 | 51.7 | 635 | 8.7 |
| 2 | 0.1 wt. % Sn | 7.7 | 64.8 | 89.4 | 57.9 | 488 | 7.4 |
| 3 | 0.1 wt. % Sn | 7.7 | 64.5 | 88.7 | 57.2 | 515 | 7.9 |
| 4 | average 0.1 wt. % Sn | 7.7 | 64.65 | 89.0 | 57.55 | 501.5 | 7.65 |

[1]stannic di-n-propyl phosphorodithioate;
[2]21,200 vanadium equivalents;
[3]25.8° API.

TABLE XV

| Run No. | Additive[1] | Cat[2]/Oil[3] Ratio | conversion (vol. %) | Selectivity to Gasoline (vol.%) | Yields Gasoline (vol. %) | $H_2$(SCF/bbl Conv.) | coke (wt. %) |
|---|---|---|---|---|---|---|---|
| 1 | None | 7.7 | 64.5 | 80.2 | 51.7 | 635 | 8.7 |
| 2 | 0.1 wt. % Sn | 7.7 | 64.7 | 89.0 | 57.6 | 502 | 7.7 |
| 3 | 0.01 Sn + 0.1 Sb | 7.7 | 70.9 | 87.6 | 62.1 | 375 | 6.9 |
| 4 | 0.1 wt. % Sb | 7.7 | 64.8 | 84.9 | 55.0 | 410 | 6.0 |

[1] stannic di-n-propylphosphorodithioate antimony di-n-phosphorodithioate;
[2] 21,200 vanadium equivalents;
[3] 25.8° API

TABLE XVI

| Run No. | Additive | Cat[2]/Oil[3] Ratio | Conversion (vol. %) | Selectivity to Gasoline (vol.%) | Yields Gasoline (vol. %) | $H_2$(SCF/bbl Conv.) | Coke (wt. %) |
|---|---|---|---|---|---|---|---|
| 1 | None | 7.7 | 64 | 83.4 | 53.3 | 640 | 8.0 |
| 2 | 0.1 wt. % Sn | 7.7 | 61.4 | 88.6 | 54.1 | 578 | 7.2 |
| 3 | 0.01 Sn + 0.1 Sb | 7.7 | 69.8 | 87.6 | 61.1 | 385 | 6.6 |
| 4 | 0.1 wt. % Sb | 7.7 | 64.8 | 85.0 | 55.0 | 410 | 6.0 |

[1] dibutyltin oxide and/or antimony di-n-propylphosphorodithioate;
[2] 21,200 vanadium equivalents;
[3] 25.8° API That which is claimed is:
1. In a process comprising:
   (a) contacting a hydrocarbon feedstock with a fluidized zeolite-containing cracking catalyst in a cracking zone under cracking conditions in the absence of added hydrogen or antimony to obtain a cracked product;
   (b) recovering the cracked product;
   (c) passing the cracking catalyst from the cracking zone to a regeneration zone;
   (d) regenerating the cracking catalyst in the regeneration zone by contact with oxygen-containing gas under regeneration conditions to produce a regenerated catalyst; and
   (e) introducing the regenerated catalyst to the cracking zone for contact with the hydrocarbon feedstock;
   wherein the regenerated catalyst contains contaminants selected from the group consisting of nickel, vanadium and iron deposited on said cracking catalyst in such a way that said cracking catalyst cannot be fully regenerated in the regeneration zone, the improvement comprising contacting the cracking catalyst with a treating agent containing tin, phosphorus and sulfur in an amount sufficient to impart to said cracking catalyst a tin concentration of from about 0.0001 to about 4 percent by weight of contacted cracking catalyst wherein the cracking catalyst is contacted with from about one-half to about 8 parts by weight of sulfur and/or from about one quarter to about one part by weight of phosphorus for each part by weight of tin with which it has been contacted.

2. A process as in claim 1 wherein the cracking catalyst is contacted with the treating agent in an amount sufficient to impart to said cracking catalyst a tin concentration of from about 0.001 to about 2 percent by weight of contacted cracking catalyst.

3. A process as in claim 2 wherein the cracking catalyst is contacted with a treating agent compound having at least one phosphorus atom and at least one sulfur atom located gamma or closer to a tin atom.

4. A process as in claim 3 wherein the cracking catalyst is contacted with a tin thiophosphate.

5. In a process comprising:
   (a) contacting a hydrocarbon feedstock with a fluidized zeolite-containing cracking catalyst in a cracking zone under cracking conditions in the absence of added hydrogen or antimony to obtain a cracked product;
   (b) recovering the cracked product;
   (c) passing the cracking catalyst from the cracking zone to a regeneration zone;
   (d) regenerating the cracking catalyst in the regeneration zone by contact with oxygen-containing gas under regeneration conditions to produce a regenerated catalyst; and
   (e) introducing the regenerated catalyst to the cracking zone for contact with the hydrocarbon feedstock;
   wherein the regenerated cracking catalyst contains contaminants selected from the group consisting of nickel, vanadium and iron deposited on said cracking catalyst in such a way that said cracking catalyst cannot be fully regenerated in the regeneration zone, the improvement comprising contacting the cracking catalyst with a treating agent represented by the formula:

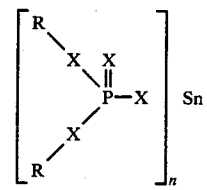

wherein each R can be the same or different and comprises a hydrocarbyl group having from 1 to about 24 carbon atoms, wherein X is selected from the group consisting of oxygen and sulfur and at least one X is sulfur, and wherein n is 2 or 4 so as to impart to the cracking catalyst a tin concentration of from about 0.0001 to about 4 percent by weight of contacted cracking catalyst.

6. A process as in claim 5 wherein the treating agent is contacted with the cracking catalyst so as to impart to said cracking catalyst a tin concentration of from about 0.001 to about 2 percent by weight of contacted cracking catalyst.

7. A process as in claim 6 wherein the treating agent is contacted with the cracking catalyst so as to impart to said cracking catalyst a tin concentration of from about 0.005 to about 1 percent by weight of contacted cracking catalyst.

8. A process as in claim 7 wherein the treating agent is contacted with the cracking catalyst so as to impart to said cracking catalyst a tin concentration of from about 0.01 to about 0.15 percent by weight of contacted cracking catalyst.

9. A process as in claim 6 wherein said treating agent is represented by the formula

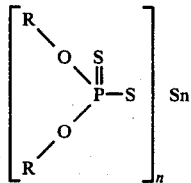

wherein R comprises a hydrocarbyl group having from 1 to about 24 carbon atoms and n is 2 or 4.

10. A process as in claim 9 wherein n equals 2 and R is selected from the group consisting of ethyl, n-propyl, isopropyl, n-butyl, isobutyl, sec-butyl, tert-butyl, amyl, n-hexyl, sec-hexyl, n-heptyl, n-octyl, isooctyl, tert-octyl, cyclopentyl, cyclohexyl, dimethylcyclohexyl, diethylcyclohexyl, phenyltolyl, cresyl, ethylphenyl, butylphenyl, amylphenyl, octylphenyl and vinylphenyl.

11. A process as in claim 9 wherein n equals 4 and R is selected from the group consisting of ethyl, n-propyl, isopropyl, n-butyl, isobutyl, sec-butyl, tert-butyl, amyl, n-hexyl, sec-hexyl, n-heptyl, n-octyl, isooctyl, tert-octyl, cyclopentyl, cyclohexyl, dimethylcyclohexyl, diethylcyclohexyl, phenyltolyl, cresyl, ethylphenyl, butylphenyl, amylphenyl, octylphenyl and vinylphenyl.

12. A process as in claim 9 wherein said treating agent is contacted with the cracking catalyst in the cracking zone.

13. A process as in claim 12 wherein said treating agent is introduced into said cracking zone in contact with the hydrocarbon feedstock.

14. A process as in claim 12 wherein said cracking catalyst has deposited thereon at least 5,000 ppm vanadium equivalents.

15. A process as in claim 14 wherein said cracking catalyst has deposited thereon at least 10,000 ppm vanadium equivalents.

16. A process as in claim 14 wherein the treating compound is contacted with the cracking catalyst so as to impart to said cracking catalyst a weight ratio of tin to vanadium equivalents on the cracking catalyst of between 0.5:100 to about 50:100.

17. A process as in claim 16 wherein the treating agent is contacted with the cracking catalyst so as to impart to the cracking catalyst a tin concentration of from about 0.005 to about 1 percent by weight of contacted cracking catalyst.

18. A process as in claim 17 wherein the treating agent is contacted with the cracking catalyst to impart to the cracking catalyst a tin concentration of from about 0.01 to about 0.15 percent by weight of contacted cracking catalyst.

19. A process as in claim 18 wherein the treating agent is dissolved in the hydrocarbon feedstock to impart to the feedstock a tin concentration of from about 1 to about 200 parts tin per million parts feedstock.

20. A process as in claim 19 wherein said treating agent comprises stannic di-n-propylphosphorodithioate.

* * * * *